United States Patent [19]
Gopakumaran et al.

[11] Patent Number: 5,827,192
[45] Date of Patent: Oct. 27, 1998

[54] METHOD OF DETERMINING THE CONDUCTIVITY OF BLOOD

[75] Inventors: Balakrishnan Gopakumaran, Cleveland, Ohio; Peter K. Osborn, West Allis, Wis.; John H. Petre, Cleveland Heights, Ohio

[73] Assignees: Cleveland Clinic Foundation, Cleveland, Ohio; Marquette Medical Systems, Milwaukee, Wis.

[21] Appl. No.: 701,177

[22] Filed: Aug. 21, 1996

[51] Int. Cl.[6] ...................................................... A61B 5/02
[52] U.S. Cl. ............................................. 600/481; 600/506
[58] Field of Search ...................................... 128/668, 673, 128/72, 642, 661.08, 713, 734, 693, 637; 600/481, 485–486, 454, 374, 526, 547, 506, 508, 381

[56] References Cited

U.S. PATENT DOCUMENTS

| | | | |
|---|---|---|---|
| 4,380,237 | 4/1983 | Newbower | 128/693 |
| 4,785,823 | 11/1988 | Eggers et al. | 128/713 X |
| 5,453,576 | 9/1995 | Krivitski | 128/668 |

OTHER PUBLICATIONS

Halliday et al., *Fundamentals of Physics*, Second Edition, 1970, (p. 548).

*Primary Examiner*—Jeffrey R. Jastrzab
*Assistant Examiner*—Ryan Carter
*Attorney, Agent, or Firm*—Michael Best & Friedrich LLP

[57] ABSTRACT

An in vivo method of determining the conductivity of a liquid such as human blood, including the steps of determining a location in a ventricle of a patient's heart at which blood conductivity may be measured effectively, positioning a catheter having a plurality of spaced electrodes in the ventricle such that at least a pair of adjacent electrodes are positioned at the location, applying a current of known magnitude to the adjacent electrodes, measuring the voltage between the adjacent electrodes, and determining the conductivity of the patient's blood from the known current and measured voltage.

6 Claims, 1 Drawing Sheet

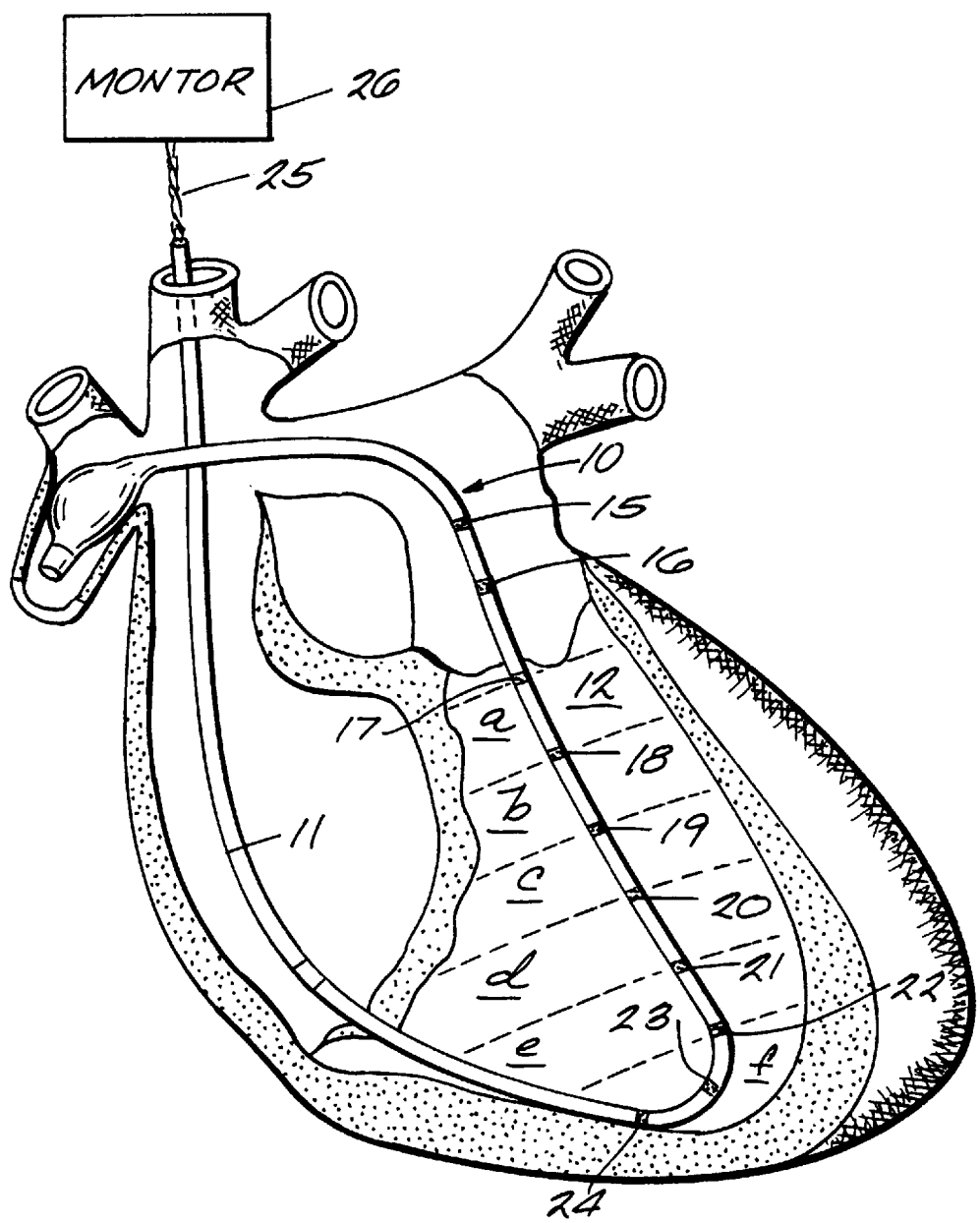

METHOD OF DETERMINING THE CONDUCTIVITY OF BLOOD

BACKGROUND OF THE INVENTION

This invention relates to cardiac monitoring and more particularly to a method of determining the electrical conductivity of blood.

One of the parameters routinely monitored in heart patients is cardiac output which is generally measured in liters per minute and corresponds to the heart's stroke volume multiplied by the heart rate. Cardiac output is particularly significant during surgery as an indication of heart performance and the adequacy of blood circulation.

There are several known methods of measuring cardiac output including thermal dilution, constant angiography and the conductance catheter method. Of these, the conductance catheter method can potentially measure the absolute ventricular volume continuously in real time and involves positioning a multi-electrode catheter in the patient's right ventricle. A constant electrical current having a fixed frequency is applied to spaced apart drive electrodes. Signals at pairs of electrodes disposed between the drive electrodes are sampled. The volume can then be computed using one of several expressions, such as for example:

$$\text{Volume} = Ih^2/Vs$$

Where:

I = the known constant current source h = the distance between sampled electrodes; and V = the voltage between sampled.

s = conductivity of the medium;

Conductive catheter methods of cardiac output measuring are disclosed in U.S. Pat. Nos. 4,674,518; 4,721,115; 4,898,176; 4,951,682 and 5,000,190.

One complicating factor with the conductance catheter method of measuring cardiac output is the determination of the conductivity of the patient's blood. The most common method is to draw the patient's blood for making conductivity measurements in a separate measuring apparatus.

SUMMARY OF THE INVENTION

It is an object of the invention to provide a new and improved method of measuring the conductivity of a medium.

A further object of the invention is to provide a new and improved method of measuring the conductivity of blood invivo for use in calculating cardiac output by the conductance catheter method.

Another object of the invention is to provide a method of monitoring cardiac output by the conductance catheter method wherein the conductivity measurement of the patient's blood is updated periodically.

These and other objects and advantages of the invention will become apparent from the detailed description of the invention taken with the accompanying drawings.

In general terms, the invention comprises a method of determining the conductivity of a liquid such as human blood, and including the steps of determining the location in a ventricle of the patent's heart at which blood conductivity can be measured effectively, positioning a catheter having at least two spaced electrodes in the ventricle of a patient's heart, positioning the electrodes proximate to said location, applying a current of known magnitude to the electrodes, measuring the voltage between the electrodes, and determining the conductivity of the patient's blood from the known current and measured voltage.

BRIEF DESCRIPTION OF THE DRAWINGS

The single FIGURE of the drawings is a sectional view of a heart showing a catheter positioned in the right ventricle.

DESCRIPTION OF THE PREFERRED EMBODIMENT

The drawing shows a conductive catheter 10 positioned in a heart ventricle 12. The Catheter 10 consists of an elongate body 11 having a plurality of axially extending lumens. The body 11 is of a flexible, plastic, insulating material and may have a stiffening member extending therethrough. A plurality of band electrodes 15–24 are mounted in an equi-spaced relation on the outer surface of the body 11. The most proximal and distal electrodes which are positioned in the ventricle are driving electrodes and the intermediate electrodes are sensing electrodes. For example, if electrodes 17–24 are inside the ventricle, then electrodes 17 and 24 may be the driving electrodes and electrodes 18–23 are sensing electrodes. Alternatively, other electrodes inwardly of those adjacent the opposite ends of the ventricle may also be employed. Individual conductors 25 are connected to each of the electrodes and extend through the lumens within body 11 and outwardly from the proximate end of catheter 10 to switching and monitoring apparatus 26 which is well known in the art.

In operation, a constant current equal to about twenty uA at two KHz is applied to the driving electrodes, such as, 17 and 24, for example. The voltage drop between successive electrodes 17–18, 18–19, 19–20, 20–21, 21–22, 22–23, and 23–24 are then measured by the monitoring apparatus 26. The volume of each of the segments between the adjacent sensing electrodes 17–24 identified in the drawing as a, b, c, d, e and f can be determined by the following expression:

$$\text{Volume of segments} = h^2 I K v/Vs$$

Where:

h = the center-to-center distance between sensing electrodes;

I = the driving current applied to electrodes 15 & 16;

Kv = a constant

V = the voltage between the sensing electrodes which define the segments a–g.

s = the conductivity of the blood within the ventricle;

The volume of the ventricle 12 is the sum of the individual volumes of the segments. For a more complete description of the conductive catheter method of measuring heart output and the apparatus for performing the same, reference is made to U.S. Pat. Nos. 4,898,176; 4,951,682 and 5,000,190; which are incorporated by reference herein.

The unknown quantity in the above expression is the blood conductivity s. Previously, blood conductivity was measured by drawing blood from the patient and measuring, conductivity separately in an auxilarily measuring apparatus. The present invention comprises the method of measuring, selecting a location in the ventricle at which conductivity can be measured effectively, selecting an adjacent pair of the sensing electrodes 17–24 proximal to the location and applying a constant current to these electrodes. Preferably the selected pair is the one which provide the best conductivity readings. The appropriate location can be determined, for example, by making a conductivity measurement between each adjacent pair of electrodes and selecting the lowest value. Another method is to look for flat peaks in the conductivity wave form which implies field saturation and thus a good reading. The voltage drop between the selected pair of electrodes is then measured. The ratio of the applied current to the measured voltage bears a constant ratio to the true conductivity of the blood. This constant calibration ratio must be determined for each specific electrode dimension and spacing and can be established by using a standard liquid of known conductivity or by computer simulation. The calibration ratio remains substantially constant as long as the electrodes are close to each other and there is a sufficient volume of blood surrounding the electrodes. Once the calibration ratio for each particular electrode dimension has been established, the true conductivity s of the blood can be determined from the following expression:

$$s = IKc/V$$

Where:
I=the applied current
Kc=the calibration ratio
V=the measured potential

If a two point current source is positioned at a unit distance apart in an infinite volume of material with uniform conductivity and the constant current injected by the source is I and the potential drop across the source is V, then it can be mathematically shown that the ratio I/V is the true conductivity of the material divided by 3.14. As a result, by multiplying the ratio I/V by 3.14 (the calibration ratio), the true conductivity of the material can be determined.

For different electrode geometry, the calibration ratio will differ from 3.14. Computer simulations and experimental evidence has shown that there is no appreciable change in the calibration ratio as long as the electrode dimensions and the material volume around the electrodes is of the order of three times or more than the electrode spacing. It has also been found that the calibration ratio is predominantly dependent on the size of the electrode rather than electrode spacing.

A typical conductance catheter has electrodes spaced about 10 mm from edge to edge. The electrodes may be about 2.5 mm in both length and diameter and may be formed of any suitable material, such as, stainless steel or an alloy of 90% platinum and 10% iridium. The catheter body is an extruded plastic material having a plurality of lumens. A plastic stiffening member is preferably disposed in one of the lumens and the conductors from the electrodes 15–24 are disposed in a different lumen.

Because the blood conductivity of a patient may change during surgery as a result of fluids which may be administered, it is desirable to update the conductivity parameter from time to time in order for the patient's cardiac output to be determined accurately. Therefore, the cardiac output monitoring may be interrupted for a short dwell period each few heartbeats by the apparatus 26 and the conductivity measurement is updated for use when the cardiac output monitoring resumes at the end of the dwell period. Alternatively, the cardiac output and conductivity measurements can be done simultaneously by employing multiplexing techniques.

Although only a single embodiment of the invention has been illustrated and described, it is not intended to be limited thereby, but only by the scope of the appended claims.

We claim:
1. In a process of determining cardiac volume by the conductance catheter method, the improvement comprising a method of determining the absolute electrical conductivity of blood as a part of said process comprising the steps of positioning in the ventricle of a mammalian heart a catheter comprising an elongate body having an outer surface and a plurality of spaced electrodes disposed on its outer surface, determining which pair of adjacent electrodes of the plurality of electrodes is optimally positioned to determine resistivity of the blood in the ventricle and selecting the pair of electrodes, applying a current of known magnitude to the selected pair of electrodes, measuring the voltage between the selected pair of electrodes and determining the absolute conductivity of the blood from the expression:

$$S = IKc/V$$

where
I=the applied current,
V=the measured voltage, and
Kc=a calibration ratio dependent upon electrode geometry and spacing.

2. The method set forth in claim 1 wherein the step of determining which pair of adjacent electrodes is optimally positioned comprises measuring the resistivity of successive pairs of adjacent electrodes and selecting the pair between which the least resistivity exists.

3. A conductive catheter method of determining cardiac volume comprising the steps of positioning a catheter in a ventricle of a patient's heart, the catheter comprising an elongate body having a proximal end and a distal end and a plurality of spaced electrodes arrayed on the outer surface thereof, said electrodes being spaced a predetermined distance from each other between the proximal and distal ends of the catheter, wherein the electrode closest to the proximal end is the proximal electrode and the electrode closest to the distal end is the distal electrode with the remaining electrodes disposed at spaced apart intervals therebetween, providing a constant alternating current to the distal and proximal electrodes located within the ventricle, measuring the potential between pairs of electrodes located between the distal and proximal electrodes disposed within the ventricle, determining cardiac volume using an expression in which the conductivity of a patient's blood is a variable, the improvement comprising the method of determining the absolute conductivity of the patient's blood and including the steps of selecting a pair of adjacent electrodes between the proximal and distal electrodes from the plurality of electrodes and which pair of adjacent electrodes are positioned optimally for making conductivity measurements, applying a current of known magnitude to the selected pair of adjacent electrodes, measuring the voltage between the selected pair of adjacent electrodes, and determining the conductivity of the patient's blood from the expression:

$$S = IKc/V$$

where
I=the applied current,
V=the measured voltage, and
Kc=a calibration ratio dependant upon electrode geometry and spacing.

4. The method set forth in claim 3 and including the steps of periodically terminating the cardiac output determination for a series of dwell periods and determining the conductivity of the patient's blood during each dwell period, and resuming the cardiac output determination at the end of each dwell period using the blood conductivity determined during the dwell period preceding the determination of cardiac output.

5. A method of determining the absolute electrical conductivity of blood comprises the steps of positioning a catheter in a patient's ventricle, the catheter comprising an elongate body having an outer surface and a plurality of spaced electrodes on the outer surface, positioning the catheter so that the plurality of electrodes are located within the ventricle, selecting a pair of adjacent electrodes between the proximal and distal electrodes from the plurality of electrodes and which pair of adjacent electrodes are positioned optimally for making conductivity measurements, applying a current of known magnitude to the selected pair of electrodes, measuring the voltage between the selected pair of electrodes and determining the conductivity of the blood from the expression:

$$S = IK_c/V$$

where

I=the applied current,

V=the measured voltage, and

Kc=a calibration ratio dependant upon electrode geometry and spacing.

6. The method set forth in claim 5 wherein the step of selecting comprises measuring the resistivity of successive pairs of adjacent electrodes and selecting the pair having the least resistivity.

* * * * *